US00PP12874P2

(12) United States Plant Patent
Zwijnenburg, Jr.

(10) Patent No.: US PP12,874 P2
(45) Date of Patent: Aug. 20, 2002

(54) HYDRANGEA PLANT NAMED 'LIMELIGHT'

(75) Inventor: Pieter Zwijnenburg, Jr., Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 09/790,773

(22) Filed: Feb. 23, 2001

(51) Int. Cl.[7] ..... A01H 5/00
(52) U.S. Cl. ..... Plt./250
(58) Field of Search ..... Plt./250

(56) References Cited

PUBLICATIONS

UPOV–ROM GTITM Computer Database, 2001/04, GTI Retrieval Software, citation for 'Limelight'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Hydrangea plant named 'Limelight', characterized by its upright flower panicles on strong peduncles with numerous flowers per panicle; unique light green-colored sepals; large calyces; and relatively early flowering.

1 Drawing Sheet

BACKGROUND OF THE INVENTION

The present Invention relates to a new and distinct cultivar of Hydrangea plant, botanically known as *Hydrangea paniculata*, and hereinafter referred to by the cultivar name Limelight.

The new Hydrangea is a product of a breeding program conducted by the Inventor in Boskoop, The Netherlands. The objective of the breeding program was to create new Hydrangea cultivars with unique flower coloration.

The new Hydrangea originated from a cross by the Inventor of two unidentified selections of *Hydrangea paniculata*, not patented. The cultivar Limelight was discovered and selected by the Inventor in the 1986 as a single plant within the progeny of the stated cross in a controlled environment in Boskoop, The Netherlands. The new Hydrangea differs from the parent selections in sepal coloration and flower size.

Asexual reproduction of the new cultivar by softwood cuttings taken at Boskoop, The Netherlands, since 1986, has shown that the unique features of this new Hydrangea are stable and reproduced true to type in successive generations.

SUMMARY OF THE INVENTION

Plants of the cultivar Limelight have not been observed under all possible environmental conditions. The phenotype may vary somewhat with variations in environment such as temperature, light intensity, daylength, irrigation amount and frequency, and fertilizer type and rate without, however, any variance in genotype.

The following traits have been repeatedly observed and are determined to be the unique characteristics of 'Limelight'. These characteristics in combination distinguish 'Limelight' as a new and distinct cultivar:

1. Upright flower panicles on strong peduncles with numerous flowers per panicle.
2. Unique light green-colored sepals.
3. Large calyces.
4. Relatively early flowering.

Plants of the new Hydrangea can be compared to plants of the *Hydrangea paniculata* cultivar Grandiflora, not patented. In side-by-side comparisons conducted in Grand Haven, Mich., plants of the new Hydrangea differ from plants of the cultivar Grandiflora in the following characteristics:

1. Sepal color of the new Hydrangea is light green whereas sepal color of the cultivar Grandiflora is white.
2. Sepals of the new Hydrangea are larger than sepals of the cultivar Grandiflora.
3. Panicles of the new Hydrangea are more upright than panicles of the cultivar Grandiflora.
4. Plants of the new Hydrangea start flowering about one month earlier than plants of the cultivar Grandiflora.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new Hydrangea. The photograph comprises a close-up view of a typical inflorescence of 'Limelight'.

DETAILED BOTANICAL DESCRIPTION

In the following description, color references are made to The Royal Horticultural Society Colour Chart, 1995 Edition, except where general terms of ordinary dictionary significance are used. Plants were grown in Grand Haven, Mich. in an uncovered greenhouse and under conditions which closely approximate commercial production conditions. Plants used for the description were grown in three-gallon containers and were about 30 months old. The description information was taken in 2000 during the summer.

Botanical classification: *Hydrangea paniculata* cultivar Limelight.

Parentage:

*Male, or pollen, parent.*—Unidentified *Hydrangea paniculata* selection, not patented.

*Female, or seed, parent.*—Unidentified *Hydrangea paniculata* selection, not patented.

Propagation:

*Type cutting.*—By softwood cuttings

*Time to intiate roots.*—Summer: About 14 days at 32° C. Winter: About 21 days at 20° C.

*Time to produce a rooted cutting or liner.*—Summer: About 56 days at 32° C. Winter: About 70 days at 20° C.

*Root description.*—Freely branching, fibrous.

Plant description:

*Crop time.*—From rooted liners, about one growing season is required to produce a flowering finished plant in a one-gallon container.

*Form.*—Upright and rounded plant habit; uniform; dense and bushy perennial shrub.

*Usage.*—Appropriate for one to three-gallon containers.

*Plant height, soil level to top of plant plane.*—About 1.8 to 2.4 meters.

*Plant diameter or area of spread.*—About 2.4 to 3 m.

*Branching habit.*—When pinched, very freely branching with about 14 lateral branches per plant.

*Lateral branches.*—Length: About 60 to 150 cm. Diameter: About 4.5 to 5 mm. Internode length: About 3 to 3.5 cm. Texture: New growth, pubescent; mature, woody growth smooth with lenticels. Lenticel quantity per linear 10 cm of stem: About 110. Lenticel length: About 1 mm. Lenticel width: About 1 mm. Color: Young stems: 60A. Mature stems: 165A. Lenticels: 165C.

*Foliage description.*—Leaves simple, opposite, generally symmetrical and long persisting. Deciduous. Quantity per lateral branch: Typically about 25. Length: About 8.5 to 10 cm. Width: About 4 to 5.5 cm. Shape: Roughly ovate. Apex: Acute. Base: Obtuse. Margin: Serrulate. Texture: Thick. Color: Young foliage, upper surface: 146B. Young foliage, lower surface: 146C. Mature foliage, upper surface: 146A; venation, 146A. Mature foliage, lower surface: 146C; venation, 196A. Petiole: Length: About 1.5 to 1.8 cm. Diameter: About 2 mm. Color: 145B tinged with 181C.

Flower description:

*Flower type and habit.*—Small star-shaped single flowers densely arranged on terminal pyramidal panicles with large showy sepals. Calyces persistent. Fragrance, not significant.

*Natural flowering season.*—Continuously flowering from mid-July to mid-October in Grand Haven, Mich.

*Flower longevity.*—Individual flowers last about 3 months on the plant and about 8 weeks as cut flowers.

*Quantity of flowers.*—Freely flowering; one terminal panicle per lateral branch with about 850 to 1,200 flowers per panicle.

*Panicle length.*—About 15 to 25 cm.

*Panicle diameter.*—About 12 to 18 cm.

*Flower diameter.*—About 2.7 to 4.7 cm.

*Flower depth.*—About 5 mm.

*Flower buds.*—Length: About 3 mm. Diameter: About 2 mm. Shape: Valvate, globulose. Color: 145A.

*Petals.*—Arrangement: About 4 to 5 in a single whorl. Length: About 3 mm. Width: About 1 to 1.5 mm. Shape: Ovate. Apex: Acute. Margin: Entire. Color: When opening, upper and lower surfaces: 145A to 145B. Fully opened, upper and lower surfaces: 145B.

*Sepals.*—Arrangement: About 4 in a single whorl. Length: About 1 to 2 cm. Width: About 0.75 to 1.25 cm. Shape: Elliptic to oval. Apex: Obtuse. Base: Attenuate. Margin: Entire. Color: When opening, upper surface: 145A. When opening, lower surface: 145A to 145B. Fully opened, upper surface: 145B. Fully opened, lower surface: 145B to 145C.

*Pedicels.*—Angle: About 80 to 90° from vertical. Strength: Strong. Length: About 1 to 1.5 cm. Diameter: About 1.5 mm. Color: 145B.

*Peduncles.*—Angle: Upright. Strength: Strong, panicles held upright. Length: About 20 cm. Diameter: About 2 to 4 mm. Color: 143B.

*Reproductive organs.*—Stamens: Quantity of stamens per flower: About 9 to 10. Anther shape: Round. Anther length: About 0.5 mm. Anther color: 145D. Pollen amount: Scarce. Pollen color: 145D. Pistils: Pistil quantity per flower: 1. Pistil length: About 0.5 to 1 mm. Stigma shape: Two to three-lobed. Stigma color: 146C. Style length: About 0.5 mm. Style color: 146C.

*Fruit.*—Type: Capsule. Length: About 5 mm. Diameter: About 2 mm. Shape: Urceolate. Color: 177B.

*Seed.*—Minute, dust-like. Length: Less than 0.5 mm. Diameter: Less than 0.5 mm. Color: Brownish.

Disease resistance: Under commercial production conditions, plants of the new Hydrangea have not been observed to be resistant to pathogens common to Hydrangea.

Temperature tolerance: Plants of the new Hydrangea have been shown to be tolerant to temperatures ranging from −38° to 38°. Plants of the new Hydrangea have been shown to be hardy to USDA Hardiness Zone 4.

It is claimed:

1. A new and distinct cultivar of Hydrangea plant named 'Limelight', as illustrated and described.

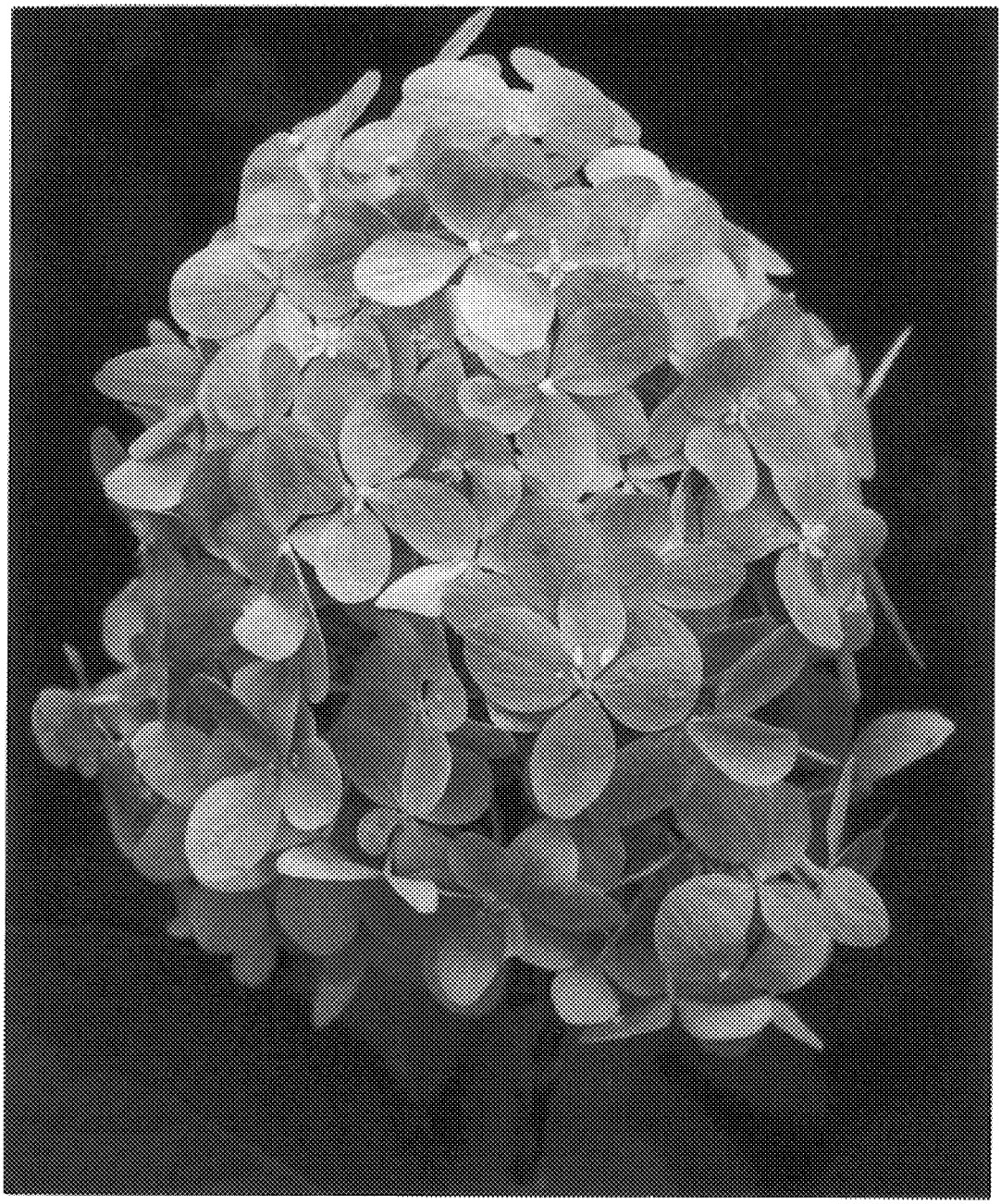

* * * * *